United States Patent [19]

Irnich

[11] Patent Number: 4,657,015

[45] Date of Patent: Apr. 14, 1987

[54] CONTROL DEVICE FOR A HIGH FREQUENCY SURGICAL APPARATUS

[76] Inventor: Werner Irnich, Birkenweg 60, D-6301 Wettenberg, Fed. Rep. of Germany

[21] Appl. No.: 701,576

[22] Filed: Feb. 14, 1985

[51] Int. Cl.⁴ .............................................. A61B 17/39
[52] U.S. Cl. ................................. 128/303.13; 128/908
[58] Field of Search ...................... 128/303.13, 303.14, 128/303.17, 908

[56] References Cited

U.S. PATENT DOCUMENTS 3,933,157  1/1976  Bjurwill et al. ................. 128/303.14
4,200,104  4/1980  Harris ............................. 128/303.14

FOREIGN PATENT DOCUMENTS 1139927  11/1962  Fed. Rep. of Germany ......................... 128/303.13
2450371  4/1975  Fed. Rep. of Germany ......................... 128/303.14
3206947  9/1983  Fed. Rep. of Germany ......................... 128/303.13

OTHER PUBLICATIONS

SRW—Nachrichten, No. 12, p. 19, 1961.

Primary Examiner—Lee S. Cohen
Attorney, Agent, or Firm—Marmorek, Guttman & Rubenstein

[57] ABSTRACT

A control device for a high frequency surgical apparatus having circuitry for sensing excessive heat build-up in body tissue is disclosed. The control device comprises a control electrode, squaring circuit, integrating circuit, comparator and a relay, whereby high frequency current is cut off when the body tissue heat build-up becomes excessive.

8 Claims, 2 Drawing Figures

U.S. Patent    Apr. 14, 1987    4,657,015
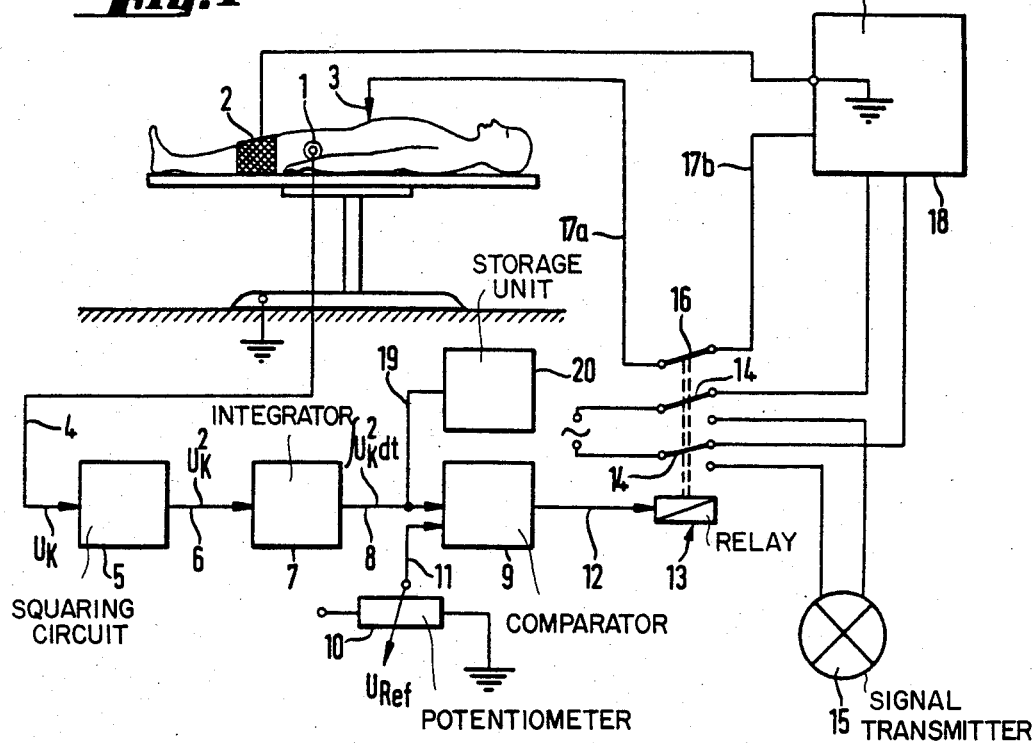
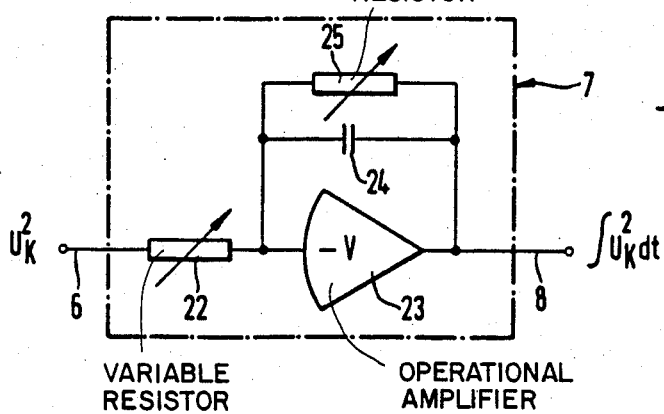

CONTROL DEVICE FOR A HIGH FREQUENCY SURGICAL APPARATUS

FIELD OF THE INVENTION

The invention relates to a control device which switches off a high frequency surgical apparatus when there is danger of burning the skin. The control device comprises a circuit which detects and measures the heat energy buildup in the body tissues and compares it with a predetermined, preset value and which switches-off the high frequency surgical apparatus when this predetermined, preset value is exceeded.

BACKGROUND OF THE INVENTION

A device of this type is known from No. DE-OS 24 50 371. In the case of this known control device, the neutral electrode is divided into two segments which are separated from one another. During the time intervals in which no high frequency current flows back to the high frequency surgical apparatus via the neutral electrode, the sum of the instantaneous resistances between the two electrode-segments and the body surface is measured; the high frequency current is shut-off when this sum exceeds, or falls below, a given range.

As, in the case of this known control device, the instantaneous resistances can be measured only in the time intervals in which no high frequency current flows, changes of the instantaneous resistances in the critical phases, that is, during the flow of the high frequency current, cannot be detected. Consequently, the danger of accidental burning is present in the case of this known control device.

SUMMARY OF THE INVENTION

The invention has as its object the creation of a control device, for high-frequency surgical apparatus, which permits the reliable determination of the danger of accidental skin burnings during an electro-surgical treatment at any point in time, in particular, even during the flowing of the high frequency current.

According to the invention, the control device comprises a control electrode, which is affixed to the body at a fairly large distance from an active electrode and which, during the treatment, picks up the high frequency voltage existing on the body with respect to the ground potential of a neutral electrode; a squaring circuit which squares the picked-up voltage; an integrator circuit which integrates the squared voltage; a comparator circuit which compares the squared, integrated, voltage with a reference voltage, and a signal transmitter and/or a relay, connected to the comparator output, which disconnects the high frequency surgical apparatus, when the integrator output exceeds a reference value.

The invention is based on the fact that a voltage existing on the body surface is an indication that there is no proper contact with a properly grounded, neutral electrode; however, the electrical voltage by itself, is not the sole determinant of the danger of becoming burned. Burning depends on the supply of electrical energy, that is, the product of the electrical field strength, the current density and the duration of application of the current.

The control device, designed according to the invention, monitors the total electrical energy which determines whether burning will take place.

The theory of operation of the control device, according to the invention, is as follows:

Injuries through overheating in the course of HF-surgery occurs when, in an area traversed by the current, the tissue thereby becomes heated to temperatures which are no longer tolerable. This is often the case, when the skin temperature rises from approximately 35° C. to 45° C. or more. This occurs when the energy per volume, also called the "volume-specific energy", delivered in several seconds, exceeds the value of 15 J/cm³.

The electrical energy per volume delivered in any given time interval is proportional to the integral, over that time interval, of the product of the electrical field strength and the current density. Analogous to Ohm's law, the proportionality between current density and field strength is defined as the specific resistance. Thus the current density can be replaced by the field strength divided by the specific resistance. Consequently, a burn can always be anticipated, when the maximum permissible volume-specific heat is equal to, or exceeded by, the time integral of a function of the square of the electrical field strength, divided by the specific resistance. Expressed as a mathematical formula, the criterion for avoidance of burns is $$\left.\frac{dW}{dV}\right|_{max} = W_{max} < \frac{1}{\rho} \int^T E^2 dt$$

where, $$\left.\frac{dW}{dV}\right|_{max} = W_{max}$$

signifies the maximum volume-specific heat which can be sustained without burning, $\rho$ signifies the specific resistance, T signifies the duration of the surgical procedure, and E signifies the electrical field strength.

At the neutral electrode, or at any point on the body which makes contact with a grounded conductor, the contact surface generally can be assumed as being large in comparison to the distance d between the metallic surface of the electrode and the trans-cutaneous tissue which is a good conductor and lies below the epidermis. Under this assumption, the electrical field strength E can be represented by the potential difference between the tissue which is a good conductor and the metallic surface of the electrode, divided by the distance between them.

This potential difference which, at a fairly large distance from the active electrode, exists between the body surface and the ground, will be designated as "body voltage" $U_K$. The previously given formula can then be transformed into:

$$W_{max} < \frac{1}{\rho d^2} \int^T U_K^2 dt$$

It is apparent from this equation, that the effective surface area of the neutral electrode or the contact surface area of the skin at the location of an accidental contact with a grounded object, does not enter into this equation, so that in the case of the control device designed in accordance with the invention, these quantities play no role. The special advantage of the device designed according to the invention, follows from this property.

Since, as a rule, the HF surgical treatments are not used continuously, but are used intermittently, a portion of the generated heat is dissipated through conduction during the ensuing intervals. Consequently, in the case of an intermittent operation, one can start from the premise that the volume-specific heat created through the integrated electrical power decreases by an amount determined by the heat dissipation in the course of the intervals of action. From the known heat-conduction equation, in which the change of the heat is assumed to be proportional to the temperature gradient, it follows that the amount by which the volume-specific heat decreases, is proportional to the time-related differential quotient of the created heat.

In an advantageous further development of the device designed according to the invention, the integrated voltage value is therefore reduced by an amount (correction factor K), which takes into consideration the quantity of heat dissipated through heat conduction in the case of intermittent operation. The amount of reduction (correction factor K) is proportional to the time-related differential quotient of the created heat and preferably is to be ascertained empirically.

The control device designed according to the invention will be explained in more detail, making reference to the accompanying drawings.

DESCRIPTION OF THE DRAWINGS

FIG. 1 shows the circuit forming the control device in the form of a block diagram, and FIG. 2 shows the circuit for the integrating stage, also as a block diagram.

DESCRIPTION OF THE PREFERRED EMBODIMENT

Referring to FIG. 1, by means of a control electrode 1, attached to the body surface of the patient and isolated from the neutral electrode 2 and any other grounded part, the body voltage $U_K$ is measured relative to the ground potential. The body voltage $U_K$ is essentially independent of the point of application of the active electrode 3 and the position of the neutral electrode 2, so that the location of the control electrode on the body surface is not critical.

The body voltage $U_K$, which is picked up by the control electrode 1 is connected to a squaring circuit 5 by means of conductor 4. The squaring circuit 5 may comprise electronic circuits known in the art, such as integrated analog squaring elements. Alternatively, the squaring circuit 5 may be a thermal convertor. A thermal convertor has the advantage that an LF-voltage is available at its output, which simplifies the following circuits.

The output, $U_K^2$, of the squaring circuit is connected to the integrator 7 via input conductor 6. Electronic integrators are readily available in the computing art. The output of integrator 7 is a voltage which is proportional to the time integral $$\int^T U_K^2 dt.$$

The integrator output is connected to the input of a comparator 9 via conductor 8. In the comparator 9, the input voltage proportional to $$\int^T U_K^2 dt$$

is compared with a reference voltage $U_{Ref}$ which can be adjusted by means of a potentiometer 10 so as to represent the maximum permissible temperature increase of each patient. Electronic comparators are widely available in the art. The comparator 9 actuates a relay 13 when the voltage proportional to $$\int^T U_K^2 dt$$

equals, or exceeds, the reference voltage $U_{Ref}$. The relay contacts 14, actuated by the relay 13, then interrupt the current supply line to the HF surgical apparatus 18, thereby shutting it off instantly. At the same time, an optical or acoustical signal transmitter 15 is switched on by the relay contacts 14. At the same time, the switching contact 16 of the relay 13 is opened, disconnecting line 17a from line 17b, thus interrupting the current to the HF surgical electrode 3 as prescribed by the regulations of the International Electrical Commission.

The output voltage of the integrator 7 can also be connected to a storage unit, a maximum-searching-unit or a recording device 20 which may be a strip chart recorder. By means of device 20, the integrated value $$\int^T U_K^2 dt$$

can be stored or recorded during the operation. These stored or recorded values can be preserved as evidence that skin efflorescences arising through the operation, could not have been caused by the HF surgery, but must have been brought about through other causes.

The integrator 7 circuitry is illustrated in FIG. 2. The input of the operational amplifier 23 is a variable resistor 22. This variable resistor 22 permits adjustment of $U_K^2$ in accordance with the individual patient-related values of the specific resistance of the body tissue, the layer-thickness d between the surface of the neutral electrode and the electrically conductive layer lying below the epidermis, and the specific thermal capacity, which determine the integration-time constants. A capacitor 24 and a variable resistance 25, are connected in parallel across the operational amplifier 23. Through this RC-circuit, the aforementioned correction factor K can be introduced, whereby the heat dissipation, in the case of intermittent operation, is taken into consideration. The individual decay constant of the thermal dissipation process can be taken into account by the adjustment of the resistance 25.

It will be apparent to those skilled in the art that various changes and modifications can be made to the disclosed preferred embodiment without departing from the spirit and scope of this invention. Accordingly, the true scope of the invention is to be determined from the following claims.

I claim:

1. A high frequency surgical apparatus including a neutral electrode adapted to be affixed to a patient's body, an active electrode adapted for surgical treatment of the patient's body, a high frequency current generator connected to the active and neutral electrodes, and a control circuit adapted to detect a high frequency voltage relative to the neutral electrode during treatment and to control the high frequency current generator in response thereto, comprising:
   (a) a control electrode adapted to be affixed to the patient's body at a large distance from said active electrode;
   (b) squaring means connected to said control electrode for squaring a voltage signal detected by said control electrode;
   (c) integrating means for integrating over time the squared voltage signal;
   (d) comparator means having a first input and a second input, said first input connected to an output of said integrating means;
   (e) a variable reference voltage source connected to said second input, for providing a predetermined reference voltage to said second input; and
   (f) switch means actuated by said comparator means for turning off said high frequency current generator, when the output voltage of said integrating means equals or exceeds said predetermined reference voltage.

2. The surgical apparatus as recited in claim 1, wherein said integrating means comprises an operational amplifier having a feedback capacitor and a variable input resistance.

3. The surgical apparatus as recited in claim 2, wherein a resistor is connected in parallel with said feedback capacitor.

4. The surgical apparatus as recited in claim 1, wherein a relay is connected to said comparator means, said relay being adapted to actuate a signal source.

5. The surgical apparatus as recited in claim 1, wherein said squaring means comprises an analog squaring element.

6. The surgical apparatus as recited in claim 1, wherein said squaring means comprises a thermal converter.

7. The surgical apparatus as recited in claim 1, wherein a memory storage device is connected to the output of said integrating means.

8. The surgical apparatus as recited in claim 7, wherein said memory storage device comprises a strip chart recorder.

* * * * *